(12) United States Patent
Murray et al.

(10) Patent No.: US 6,994,684 B2
(45) Date of Patent: Feb. 7, 2006

(54) PUNCTUM PLUGS HAVING FLUID COLLECTING RECESSES AND METHODS OF PUNCTAL OCCLUSION

(75) Inventors: George W. Murray, Germantown, TN (US); Michael J. Watermeier, Memphis, TN (US)

(73) Assignee: AlphaMed Inc., El Paso, TX (US)

( * ) Notice: Subject to any disclaimer, the term of this patent is extended or adjusted under 35 U.S.C. 154(b) by 406 days.

(21) Appl. No.: 10/461,684

(22) Filed: Jun. 16, 2003

(65) Prior Publication Data

US 2004/0254516 A1    Dec. 16, 2004

(51) Int. Cl.
*A61M 5/00* (2006.01)
*A61M 35/00* (2006.01)
*A61F 2/04* (2006.01)
*A61F 11/00* (2006.01)

(52) U.S. Cl. ............. 604/8; 604/294; 623/23.64; 606/108

(58) Field of Classification Search ............. 604/8–10, 604/500, 521, 19, 27, 28, 264, 294, 298, 604/289–290, 540–541, 523, 317, 285, 907; 66/107–108, 185, 167, 191, 109; 623/11.11, 623/4.1, 23.64, 23.71; 128/887
See application file for complete search history.

(56) References Cited

U.S. PATENT DOCUMENTS

| | | | |
|---|---|---|---|
| 3,949,750 A | 4/1976 | Freeman |
| 4,660,546 A | 4/1987 | Herrick et al. |
| 4,915,684 A | 4/1990 | MacKeen et al. |
| 4,955,896 A | 9/1990 | Freeman |
| 4,959,048 A | 9/1990 | Seder et al. |
| 5,049,142 A | 9/1991 | Herrick et al. |
| 5,163,959 A | 11/1992 | Herrick |
| 5,171,270 A | 12/1992 | Herrick |
| 5,283,063 A | 2/1994 | Freeman |
| 5,334,137 A | 8/1994 | Freeman |
| 5,417,651 A | 5/1995 | Guena et al. |
| 5,423,777 A | 6/1995 | Tajiri et al. |
| 5,723,005 A | 3/1998 | Herrick |
| 5,741,292 A | 4/1998 | Mendius |
| 5,830,171 A | 11/1998 | Wallace |
| 6,016,806 A | 1/2000 | Webb |
| 6,027,470 A | 2/2000 | Mendius |
| 6,041,785 A | 3/2000 | Webb |
| 6,149,684 A | 11/2000 | Herrick |
| 6,234,175 B1 | 5/2001 | Zhou et al. |
| 6,290,684 B1 | 9/2001 | Herrick |
| 6,306,114 B1 | 10/2001 | Freeman et al. |
| 6,344,047 B1 | 2/2002 | Price et al. |
| 6,527,780 B1 | 3/2003 | Wallace et al. |

*Primary Examiner*—Patricia Bianco
(74) *Attorney, Agent, or Firm*—D'Ambrosio & Associates, P.L.L.C.

(57) ABSTRACT

A punctum plug includes a distal tip, a proximal cap and a body connecting the tip to the cap. The cap has a proximal surface which remains exposed in the eye upon implantation of the punctum plug. A passage for an insertion tool extends distally in the punctum plug from an opening along the proximal surface. One or more recesses in the proximal surface collect tear fluid by surface tension, and each recess is laterally offset in its entirety from the opening and does not overlap or align with the opening. The number of recesses is indicative of the size of the punctum plug. A method of punctal occlusion involves collecting tear fluid in the one or more recesses and adhering the tear fluid in the one or more recesses by surface tension.

21 Claims, 6 Drawing Sheets

PUNCTUM PLUGS HAVING FLUID COLLECTING RECESSES AND METHODS OF PUNCTAL OCCLUSION

BACKGROUND OF THE INVENTION

1. Field of the Invention

The present invention relates generally to the treatment of tear fluid deficiencies in the eye and, more particularly, to punctum plugs and methods of punctal occlusion for deterring the drainage of tear fluid from the eye.

2. Brief Discussion of the Related Art

Normally the eye is protected and lubricated by a film of naturally produced tear fluid spread over the corneal and conjunctival epithelia through blinking. Various problems may arise in the eye, however, where the quantity of tear fluid in the eye is deficient, and such problems may be referred to generally as dry eye syndrome. Tear fluid deficiencies are oftentimes chronic and may result from inadequate tear fluid production and/or drainage of too much tear fluid from the eye through the lacrimal drainage system of the eye. Various conditions may cause and/or aggravate tear fluid deficiencies including disease, inflammation, congenital defects, side effects of over-the-counter and prescription drugs, environmental irritants or effects, atrophy, aging, eye strain, and procedures performed on the eye such as Lasik and cataract procedures.

Dry eye syndrome is increasing in prevalence and it is estimated that up to 40% of the U.S. population suffers from dry eye syndrome to some extent. Dry eye syndrome may manifest as various ophthalmic ailments including itchy, gritty, sticky and/or burning sensations, conjunctivitis, blepharitis, contact lens problems, corneal erosion, incipient corneal graft rejection, recurrent chalzion, pinguecula, corneal ulcers and acute lid abscesses. Sinus ailments, hay fevers, colds and other recurrent infections have been attributed to dry eye syndrome.

One common treatment for dry eye syndrome involves the introduction of artificial tear fluid into the eye. The benefits derived from artificial tear fluids are limited and are usually of short duration. In some users, artificial tear fluids have caused toxic reactions. Other drawbacks of artificial tear fluids include possible blurred vision and unsightly deposits on the eyelids.

Mechanical devices such as punctum plugs which block or occlude the puncta to deter drainage of tear fluid from the eye have been proposed and are represented by U.S. Pat. Nos. 3,949,750 and 5,283,063 to Freeman, U.S. Pat. No. 4,915,684 to MacKeen et al, U.S. Pat. No. 4,959,048 to Seder et al, U.S. Pat. Nos. 5,723,005, 6,149,684 and 6,290,684 B1 to Herrick, U.S. Pat. No. 5,417,651 to Guena et al, U.S. Pat. No. 5,423,777 to Tajiri et al, U.S. Pat. Nos. 5,741,292 and 6,027,470 to Mendius, U.S. Pat. No. 5,830,171 to Wallace, U.S. Pat. Nos. 6,016,806 and 6,041,785 to Webb, U.S. Pat. No. 6,234,175 B1 to Zhou et al, U.S. Pat. No. 6,306,114 B1 to Freeman et al, and U.S. Pat. No. 6,344,047 B1 to Price et al.

Punctum plugs typically include a proximal head, a distal tip and a shaft connecting the proximal head and the distal tip. The shaft is often smaller in cross-sectional size than the proximal head and the distal tip. A punctum plug is usually inserted, distal tip first, in a punctal opening of the punctum and is advanced distally in the punctum until the proximal head is seated on the punctal opening. The proximal head is normally larger than the punctal opening such that the proximal head does not pass through the punctal opening and remains exposed in the eye. The distal tip typically has a cross-sectional size to fill the canalicular canal which is in communication with the punctal opening and to anchor the punctum plug in place. Usually the proximal head overlaps and is in abutment with a rim of anatomical tissue circumscribing the punctal opening. The blockage or occlusion presented by the punctum plug deters tear fluid from draining from the eye through the punctal opening and the corresponding canalicular canal from which tear fluid would otherwise drain into the lacrimal sac and through the nasolacrimal duct into the nasal cavity.

Typically, punctum plugs are implanted in the eye using insertion tools, and punctum plugs having axial passages for releasably engaging the insertion tools to facilitate or guide implantation have been proposed as represented by U.S. Pat. No. 3,949,750 to Freeman, U.S. Pat. No. 4,915,684 to MacKeen et al, U.S. Pat. No. 5,171,270 to Herrick, U.S. Pat. Nos. 5,283,063 and 5,334,137 to Freeman, U.S. Pat. No. 5,423,777 to Tajiri et al, U.S. Pat. No. 5,723,005 to Herrick, U.S. Pat. Nos. 5,741,292 and 6,027,470 to Mendius, U.S. Pat. No. 5,830,171 to Wallace, U.S. Pat. No. 6,016,806 to Webb, U.S. Pat. No. 6,149,684 to Herrick, U.S. Pat. No. 6,306,114 B1 to Freeman et al, and U.S. Pat. No. 6,344,047 B1 to Price et al, and U.S. Pat. No. 6,527,780 B1 to Wallace et al.

The proximal heads of the punctum plugs remaining exposed in the eye may be engaged with the insertion tools or other instruments by which the punctum plugs may be withdrawn from the punctal openings for removal from the eye. The proximal heads thusly enhance the ease with which punctum plugs may be implanted in and removed from the eye and enable greater patient comfort and safety during implantation and removal. Furthermore, the proximal heads facilitate proper positioning of the punctum plugs in the eye and inhibit displacement of the punctum plugs by preventing the punctum plugs from being advanced too far in the puncta. Disadvantageously, however, the exposed proximal heads of conventional punctum plugs may cause corneal irritation and/or lid sensation in patients, resulting in discomfort and/or intolerance for many patients. Attempts have been made to avoid corneal irritation and/or lid sensation by reducing the profile or thickness of the proximal heads; however, structural strength and integrity are thereby sacrificed. The axial passages of conventional punctum plugs are not useful to retain tear fluid on the proximal heads of the punctum plugs for exposure in the eye due to the axial passages being of appreciable length.

Intracanalicular implants have been proposed which are disposed entirely within the canalicular canal without exposure or protrusion thereof in the eye, and such implants are illustrated by U.S. Pat. Nos. 4,660,546, 5,049,142 and 5,053,030 to Herrick et al and U.S. Pat. Nos. 5,163,959 and 5,171,270 to Herrick. Intracanalicular implants which are disposed entirely within the canalicular canal are more difficult to implant and remove and are more likely to be implanted improperly or to become displaced in the canalicular canal.

Conventional punctum plugs may be made available in different sizes corresponding to anatomical puncta and canaliculi of different cross-sectional sizes. Since the anatomical puncta and canaliculi are of microscopic size, punctum plugs are also of microscopic size. Consequently, it is very difficult to distinguish between different size punctum plugs, and it is particularly difficult to visually ascertain the size of a punctum plug while implanted in the eye.

Accordingly, there is a need for a punctum plug having a proximal head or cap which remains exposed in the eye following implantation of the punctum plug while reducing the potential for corneal irritation and/or lid sensation from the exposed cap. A need exists for a punctum plug having a cap which retains tear fluid thereon for wetting the cornea when the cap is exposed in the eye after implantation of the punctum plug in the eye. There is also a need for a punctum plug in which tear fluid is collected in and adheres to a cap of the punctum plug via surface tension of the tear fluid in one or more shallow recesses of the cap. Another need exists for a punctum plug that enables size identification of the punctum plug to be accomplished through visualization of a cap of the punctum plug while the punctum plug is or is not implanted in the eye.

SUMMARY OF THE INVENTION

Accordingly, it is an object of the present invention to overcome the aforementioned disadvantages of prior punctum plugs and methods of punctal occlusion.

Another object of the present invention is to reduce the potential for corneal irritation and/or lid sensation in patients with implanted punctum plugs having caps exposed in the eye.

A further object of the present invention is to improve eye comfort in patients with implanted punctum plugs having caps exposed in the eye.

It is also an object of the present invention to increase patient tolerance for punctum plugs having caps which remain exposed in the eye.

The present invention has as an additional object to retain tear fluid on a cap of a punctum plug for enhanced wetting of the cornea when the cap remains exposed in the eye after implantation of the punctum plug in the eye.

An additional object of the present invention is to collect and adhere tear fluid in a cap of a punctum plug by surface tension of the tear fluid in one or more shallow recesses of the cap.

Yet another object of the present invention is to enable size identification of a punctum plug through visualization of a cap of the punctum plug while the punctum plug is or is not implanted in the eye.

The present invention also has as an object to permit visual size identification of an implanted punctum plug without removing the punctum plug from the eye.

Still a further object of the present invention is to enable size identification of a punctum plug from the number of recesses in a cap of the punctum plug.

The aforesaid objects are achieved individually and in combination, and it is not intended that the present invention be construed as requiring two or more of the objects to be combined unless expressly required by the claims attached hereto.

Some of the advantages of the present invention are that a greater number of patients can be treated for dry eye syndrome by punctal occlusion with greater patient comfort and tolerance; greater patient comfort and tolerance are achieved without sacrificing structural integrity ans strength of the punctum plugs; various insertion tools or instruments can be used to implant the punctum plugs in and remove the punctum plugs from the eye; the caps of the punctum plugs facilitate proper implantation and inhibit displacement of the punctum plugs by ensuring the punctum plugs are inserted to the proper depth; the caps facilitate proper placement of the punctum plugs by abutment with the anatomical tissue circumscribing the punctal openings; the caps provide accessible structure for promoting engagement of the punctum plugs with insertion tools or instruments for implantation and/or removal of the punctum plugs from the eye; the punctum plugs can be implanted and removed without trauma to patients; the distal tips of the punctum plugs promote advancement of the punctum plugs during implantation and inhibit withdrawal of the punctum plugs after implantation; the punctum plugs can be economically manufactured of medically acceptable silicon rubber; the number of recesses in the caps of the punctum plugs may vary; the geometric configuration of the recesses may vary; the one or more recesses may be arranged on the caps in various ways; tear fluid collected by the recesses is maintained close to the cornea for more effective wetting of the corneal surface; the punctum plugs can be safely implanted in and removed from patients' eyes as office procedures performed by trained eye technicians or eye care medical professionals; implantation and removal are safe and pain free for patients; the punctum plugs can be economically produced using various manufacturing processes and equipment; and the punctum plugs can remain implanted for various lengths of time.

These and other objects, advantages and benefits are realized with the present invention as generally characterized in a punctum plug for implantation in the lacrimal drainage system of the eye. The punctum plug comprises a distal tip, a proximal cap and a body connecting the distal tip to the proximal cap. The distal tip comprises an anchor having a configuration facilitating advancement of the punctum plug in a punctal opening of the lacrimal drainage system and into the canalicular canal communicating with the punctal opening. The anchor has a configuration to apply force or pressure against the anatomical wall of the canalicular canal to resist removal or withdrawal of the punctum plug. The cap seats over the punctal opening when the punctum plug is implanted and blocks or occludes the punctal opening to prevent or inhibit drainage of tear fluid through the punctal opening from the eye. A proximal surface of the cap remains exposed in the eye when the punctum plug is implanted, and the cap abuts anatomical tissue circumscribing the punctal opening to ensure insertion of the punctum plug to the proper depth. The punctum plug comprises an insertion passage for releasably engagement with an insertion tool, the passage extending in the distal direction from an opening along the proximal surface. One or more fluid collecting recesses are disposed along the proximal surface for collecting tear fluid. Each recess has a periphery along the proximal surface and a curved floor joined to the proximal surface along the periphery. The floor extends below the proximal surface to a shallow depth, and the entire area circumscribed by the periphery is enclosed by the floor. Each recess has a center laterally offset from the central longitudinal axis of the insertion passage. The opening of the insertion passage has a perimeter along the proximal surface, and the perimeter is disposed in its entirety outside of the periphery of each recess. Accordingly, each recess is laterally offset in its entirety from the opening and does not overlap or align with the opening. The punctum plug may be made available in different sizes with each size punctum plug having a different number of recesses. Size identification—of a punctum plug can thusly be made visually by noting the number of recesses in the proximal surface of the cap. Since the proximal surface remains exposed in the eye when the punctum plug is implemented, size identification can be accomplished while the punctum plug is implanted.

The present invention is further generally characterized in a method of punctal occlusion involving the steps of releasably engaging an insertion tool in an insertion passage of a punctum plug having a distal tip, a proximal cap and a body connecting the distal tip to the proximal cap with the insertion passage extending distally in the punctum plug from an opening along a proximal surface of the cap, introducing the distal tip through a punctal opening, advancing the punctum plug in the punctal opening to anchor the tip in the canalicular canal communicating with the punctal opening and to seat the cap over the punctal opening with the proximal surface exposed in the eye, withdrawing the insertion tool from the eye, leaving the punctum plug in place to block drainage of tear fluid from the eye, collecting tear fluid in one or more recesses in the proximal surface in which each of the recesses is non-overlapping with the opening, and adhering the tear fluid in the one or more recesses by surface tension. The step of advancing may include limiting advancement of the punctum plug via engagement or abutment of the cap with anatomical tissue circumscribing the punctal opening. The step of leaving may include anchoring the punctum plug in place via engagement of the tip with the anatomical wall of the canalicular canal. The method may further include, subsequent to the step of leaving, the steps of visualizing the proximal surface exposed in the eye, noting the number of recesses in the proximal surface and identifying the size of the punctum plug from the number of recesses.

These and other objects, advantages and benefits of the present invention will become apparent from the following description of the preferred embodiments taken in conjunction with the accompanying drawings wherein like parts in each of the several figures are identified by the same reference characters.

DESCRIPTION OF THE PREFERRED EMBODIMENTS

Figure 1:
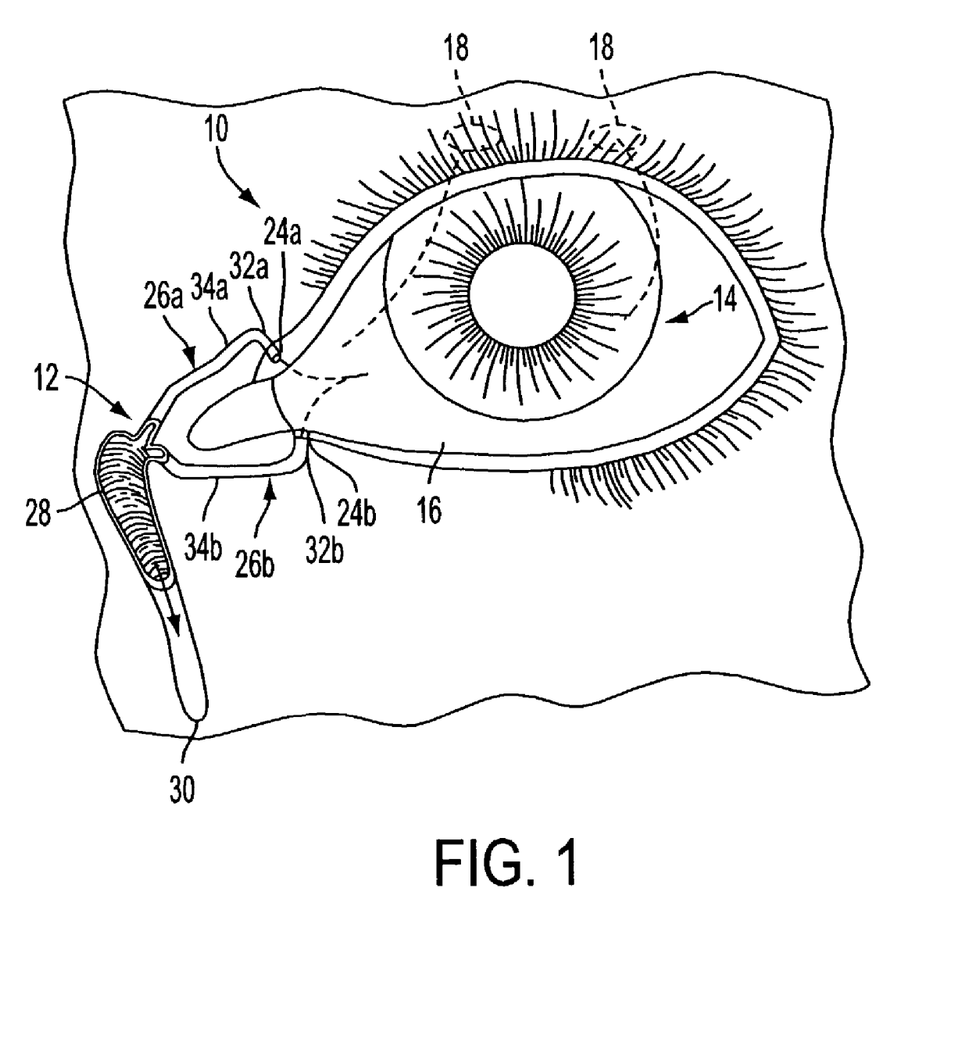
FIG. 1 is an anatomical representation of the lacrimal drainage system of the eye.

FIG. 1 depicts an eye 10 and its lacrimal drainage system 12. Eye 10 comprises eyeball 14 having cornea 16. A series of small lacrimal glands 18 spaced apart from one another above cornea 16 produce constant tears, and a large lacrimal gland 20 produces crying tears. The cornea 16 and the inner surfaces of the eyelids are moisturized and lubricated by tear fluid, which forms a tear film over the cornea 16. The tear film serves to wet and lubricate the eye through a balance of an outer lipid (oily) layer, a middle aqueous (watery) layer and an inner mucin (mucous) layer. Tear fluid drains from the eye through the lacrimal drainage system 12 comprising upper punctum and lower punctum having upper and lower punctal openings 24a and 24b, respectively, communicating with respective upper and lower canalicular canals 26a and 26b leading to lacrimal sac 28 having nasolacrimal duct 30. The upper and lower punctal openings 24a and 24b are located at the inner corners of the upper and lower eyelids, respectively, and are each circumscribed by a rim of anatomical tissue. Tear fluid drains from the eye through the punctal openings 24a and 24b, the upper and lower canalicular canals 26a and 26b, the lacrimal sac 28 and the nasolacrimal duct 30 into the nasal cavity. The majority of tear fluid drains through the lower punctum, the upper and lower canalicular canals 26a and 26b comprise vertical canalicular portions 32a and 32b extending from the punctal openings 24a and 24b, respectively, to horizontal canalicular canal portions 34a and 34b, respectively, extending to the lacrimal sac 28.

Figure 2:
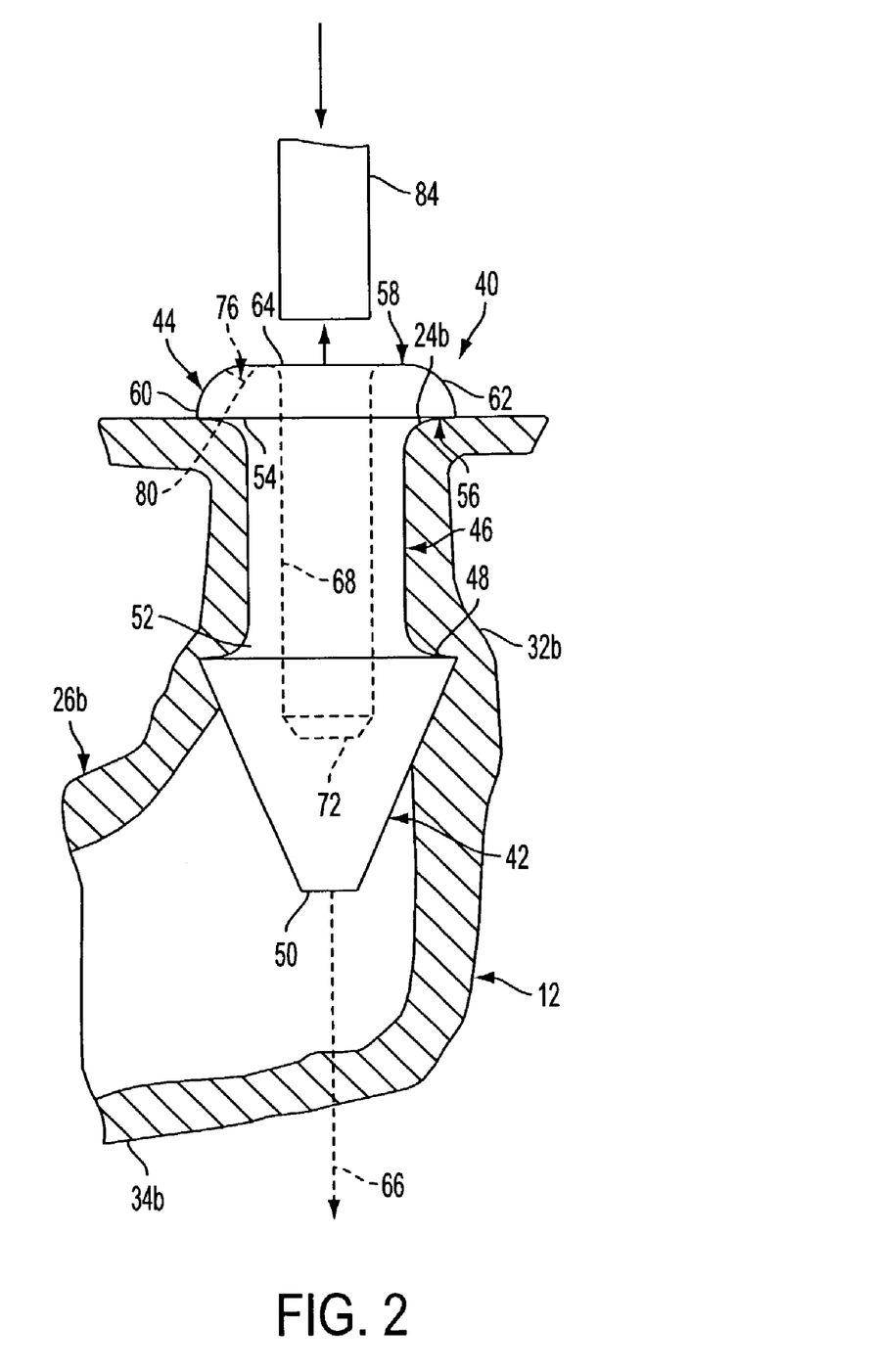
FIG. 2 is a broken side view, partly in section, of the lacrimal drainage system with a punctum plug according to the present invention implanted therein.
Figure 3:
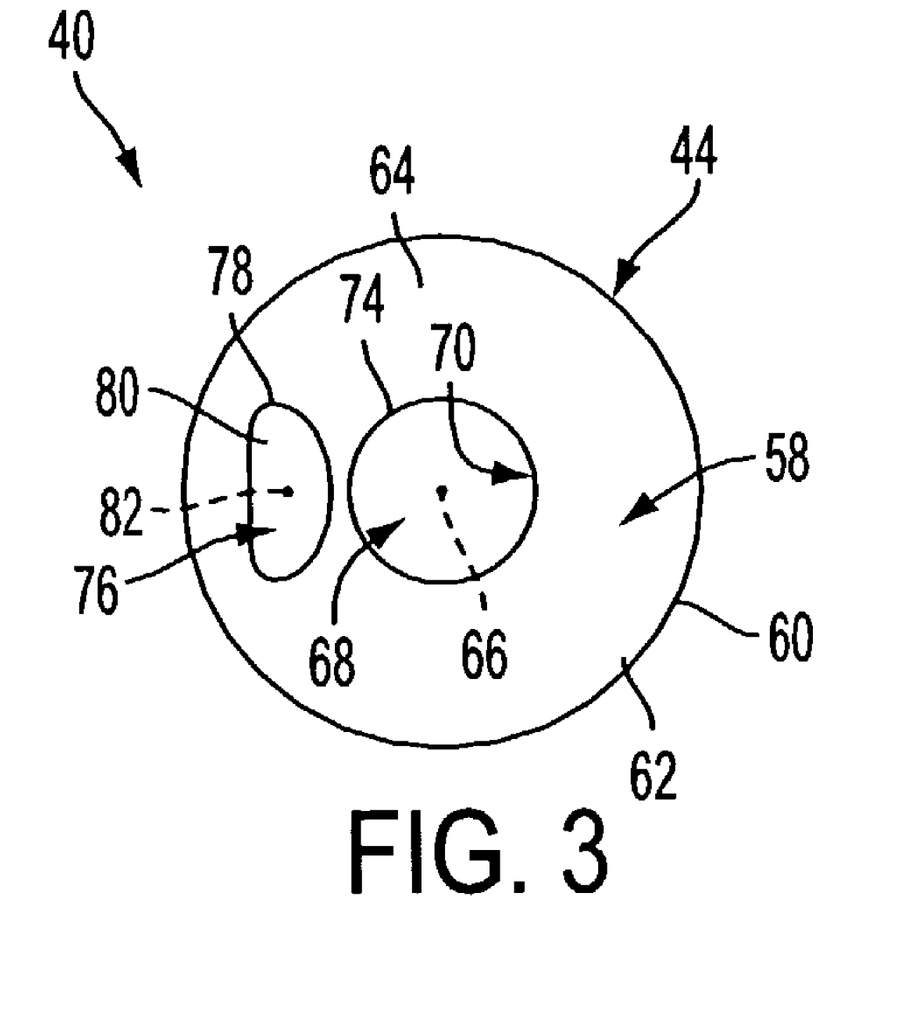
FIG. 3 is a top view of the punctum plug of FIG. 2.

A punctum plug 40 according to the present invention is shown in FIGS. 2 and 3, the punctum plug 40 being depicted in FIG. 2 implanted in the lacrimal drainage system 12 to block the drainage of tear fluid from the eye 10 via the lacrimal drainage system. The punctum plug 40 comprises a distal tip 42, a proximal cap 44, and a body 46 connecting the tip 42 to the cap 44. The tip 42 comprises an anchor of frustoconical configuration having a circular external cross-section continuously tapering from a maximum external diameter at a rearward end 48 to a minimum external diameter at a forward end 50. The rearward end 48 of tip 42 includes a planar surface, and the forward end 50 of tip 42 includes a planar surface parallel to the planar surface of rearward end 48. The body 46 extends longitudinally from tip 42 to cap 44 and is essentially cylindrical in external configuration with a uniform or constant circular external cross-section between flared forward and rearward ends 52 and 54 at which the body is joined to the tip 42 and the cap 44, respectively. The external cross-sectional diameter of the body 46 is less than the maximum external diameter of tip 42. The cap 44 has a distal surface 56 joined to the rearward end 54 of body 46 and has a proximal surface 58. The distal surface 56 is planar about the rearward end 54 of body 46 and has a perimetrical edge 60 of circular configuration with a diameter greater than the external cross-sectional diameter of body 46. The proximal surface 58 is joined to the distal surface 56 at perimetrical edge 60, which circumscribes the proximal surface and defines an external perimeter for cap 44 and proximal surface 58. The proximal surface 58 comprises an annular border 62 along perimetrical edge 60, the annular border 62 having a surface continuously curving from perimetrical edge 60 to a central portion 64 of proximal surface 58. The central portion 64 is circumscribed by the annular border 62 and comprises a planar surface parallel to the planar surface of distal surface 56. The tip 42, cap 44 and body 46 are concentric with one another and coaxial with a central longitudinal axis 66 of the punctum plug.

A longitudinal passage 68 extends distally within the punctum plug 40 from proximal surface 58 to terminate within tip 42 such that the body 46 may be considered a tube. The passage 68 is coaxial with the central longitudinal axis 66 and has an opening 70 along proximal surface 58, the opening 70 being disposed along the central portion 64 of proximal surface 58. The passage 68 is essentially cylindrical in configuration with a uniform circular cross-section extending longitudinally from a flared mouth at opening 70 to a beveled bottom 72 in tip 42. The opening 70 has a perimeter 74 of circular geometric configuration along central portion 64 of proximal surface 58. The passage 68 provides an insertion passage for releasably engaging a portion of an insertion tool inserted in the passage to facilitate and guide insertion or implantation of the punctum plug 40 in the lacrimal drainage system as explained further below. The passage 68 also enhances the ability of body 46 to resiliently flex or deform to the anatomical contour of the canalicular canal in which the punctum plug is implanted.

The punctum plug 40 comprises one or more fluid collecting recesses 76 in the proximal surface 58 of cap 44 for retaining tear fluid, and the punctum plug 40 is shown as having one recess 76. The recess 76 has a periphery 78 along proximal surface 58, the periphery 78 being disposed along the central portion 64 so as to be coplanar with the perimeter 74 of opening 60. The entire area within or circumscribed by periphery 78 is enclosed by a floor 80 of recess 76 which is joined to the central portion 64 along periphery 78. The floor 80 presents a solid surface along the entire area within periphery 78 and is inwardly or concavely curved to a shallow depth below proximal surface 58 for collecting tear fluid as described further below. The periphery 78 can have various geometric configurations and is depicted by way of example in FIG. 3 as having a partial-circular or semi-circular geometric configuration with a straight side and a curved side joined to the straight side at rounded corners. The recess 76 has a center or central axis 82, and the center 82 is laterally offset or spaced from the central longitudinal axis 66. The entire periphery 78 is disposed along proximal surface 58 outside of the perimeter 74. Accordingly, the recess 76 is not in axial communication or alignment with the passage 68 or its opening 70 and is not axially aligned with the central longitudinal axis 66. The entire periphery 78 and floor 80 of recess 76 are laterally offset from and do not overlap or align with the perimeter 74 or opening 70. The recess 76 is thusly separate and distinct from the opening 70 and is not coextensive with the opening 70.

The recess 76 can be arranged on the proximal surface 58 in various ways. As an example, the recess 76 is arranged on the proximal surface 58 with the center 82 thereof disposed along a radial line emanating from with the central longitudinal axis 66, with the straight side of periphery 78 perpendicular to this radial line, and with the curved side of the periphery 78 disposed closer to the axis 66 than the straight side thereof.

The punctum plug 40 is preferably made in its entirety of a biocompatible or medically acceptable rubber such as silicone rubber. One example of a suitable silicone rubber is NUSIL silicone of 70 durometer, and typical durometers may be in the range of 60–70 Shore A durometer. Various manufacturing equipment and processes may be used to fabricate the punctum plug including various micro-molding equipment and processes such as individual compression silicone molding, liquid silicone injection molding and multi-cavity compression molding. A virtually "flash free" product can be produced whereby additional deflashing, trimming and handling can be eliminated for a reduction in cost. The punctum plug 40 will typically be supplied to medical service providers in a medically sterile condition ready for implantation.

The punctum plug 40 is implanted in the lacrimal drainage system 12 by being inserted, tip 42 first, into a punctal opening such as lower punctal opening 24b shown in FIGS. 1 and 2. The punctum plug 40 is advanced distally or forwardly in the punctal opening 24b until the cap 44 is seated on or over the punctal opening 24b and the tip 42 is disposed in the canalicular canal 26b communicating with the punctal opening 24b as depicted in FIG. 2. The tapered configuration of the tip 42 promotes advancement of the punctum plug without trauma or pain for the patient, and the tip 42 centers and aligns the punctum plug in the canalicular canal during insertion. As shown in FIG. 2, a distal end of an insertion tool 84 may be removably engaged in the passage 68 with the proximal end of the insertion tool being grasped and manipulated to control the position and movement of the punctum plug during implantation. Upon implantation of the punctum plug 40, the insertion tool 84 is disengaged therefrom leaving the implanted punctum plug in place in the lacrimal drainage system 12.

The punctum plug 40 is shown implanted in FIG. 2 with the distal surface 56 of cap 44 in abutment with is seated against the rim of anatomical tissue circumscribing or surrounding the punctal opening 24b, and the distal surface 56 is larger than the punctal opening 24b to prevent the cap 44 from passing therethrough. The cap 44 covers the punctal opening 24b in its entirety and blocks or occludes the punctal opening to prevent or deter tear fluid from passing through the punctal opening from the eye. Engagement or abutment of the cap 44 with the anatomical rim of the punctal opening 24b limits and controls the distance that the punctum plug 40 may be advanced during implantation so that proper implantation is ensured. The rearward end 48 of tip 42 is of a size to forcefully engage the anatomical wall of the canalicular canal 26b to prevent the punctum plug 40 from moving proximally or rearwardly. Accordingly, the punctum plug 40 is anchored or secured in place in the lacrimal drainage system 12. Although the tip 42 is depicted as being anchored in the vertical canalicular canal portion 32b, it should be appreciated that the tip can extend into and/or be anchored within the horizontal canalicular canal portion 34b. Of course, the anchoring force or pressure provided by tip 42 on the wall of canalicular canal 26b can be overcome when the punctum plug 40 is forcefully withdrawn from the canalicular canal through the punctal opening 24b for removal from the eye. The body 46 may resiliently flex or deform to accommodate the anatomical contour of the canalicular canal 26b, and the body 46 is of a cross-sectional size to fit through the punctal opening 24b.

The recess 76 collects tear fluid of the eye and adheres the tear fluid by surface tension of the tear fluid. The shallow depth of the recess 76 promotes collection of tear fluid for disposition along proximal surface 58 so that the collected tear fluid is exposed in the eye to provide wetting and lubrication for the cornea 16. The wetting and lubrication provided by tear fluid collected in recess 76 assists in keeping the cornea 16 wetted and reduces possible lid sensation due to the cap 44 being exposed in the eye. The punctum plug 40 provides greater comfort for the patient and increased tolerance to the punctum plug such that the punctum plug can remain in place for longer periods of time. Greater comfort and increased tolerance are achieved without having to reduce the thickness or profile of the cap so that structural integrity and strength are not sacrificed.

In a representative but not limiting embodiment of punctum plug 40, the punctum plug has an overall length of about 0.055 inch; the tip has a length of about 0.023 inch, a maximum external diameter of about 0.026 inch and a minimum external diameter of about 0.005 inch; the body has a length of about 0.027 inch and an external cross-sectional diameter of about 0.016 inch with the flared forward and rearward ends having a radius of curvature of about 0.003 inch; the passage has a length of about 0.040 inch and a diameter of about 0.0090 inch; the cap has a thickness of about 0.005 inch and a perimetrical edge about 0.026 inch in diameter with the annular border having a radius of curvature of about 0.004 inch; the perimeter of the opening is about 0.0090 inch in diameter; the recess has a depth of about 0.001 inch; and the periphery of the recess has a major dimension of about 0.008 inch and a minor dimension of about 0.004 inch with the periphery of the recess spaced along the proximal surface about 0.001 inch from the perimeter of the opening. The representative dimensions for punctum plug 40 may be considered illustrative of an "extra small" size punctum plug. As described further below, the punctum plugs according to the present invention may be made available in different sizes corresponding to different anatomical sizes of punctal openings and canalicular canals.

Figure 4:
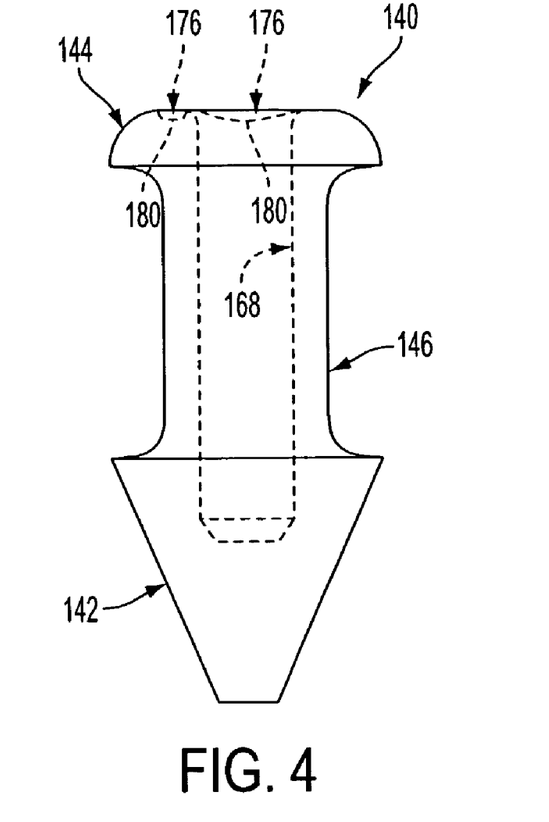
FIG. 4 is a side view of an alternative punctum plug according to the present invention.
Figure 5:
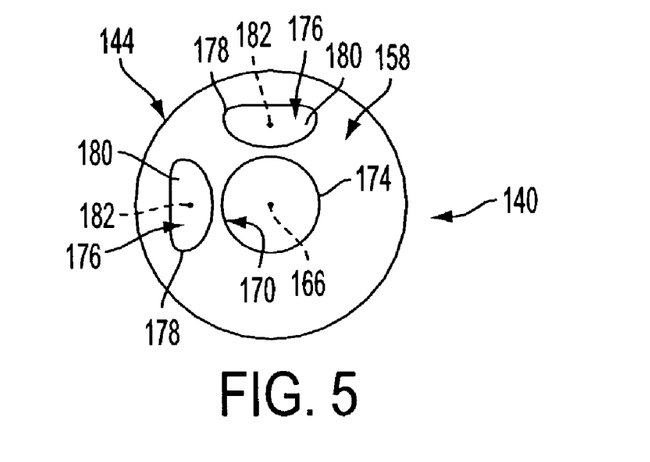
FIG. 5 is a top view of the punctum plug of FIG. 4.

Another punctum plug according to the present invention is depicted at 140 in FIGS. 4 and 5. Punctum plug 140 is similar to punctum plug 40 and comprises distal tip 142, proximal cap 144, body 146 and passage 168. Punctum plug 140 differs from punctum plug 40 in that the proximal surface 158 of cap 144 has two recesses 176 separate and distinct from each other and from opening 170 of passage 168. Recesses 176 are each similar to recess 76 and have centers 182 laterally offset from the central longitudinal axis 166 of punctum plug 140. Each recess 176 has the entire area circumscribed by its periphery 178 enclosed by the floor 180 of the recess. The entire periphery 178 of each recess 176 is disposed along proximal surface 158 outside of the perimeter 174 of opening 170 along proximal surface 158. Accordingly, the entirety of each recess 176 is not coextensive with and does not overlap the opening 170. Also, there is no overlap or coextensiveness between the peripheries 178 of the recesses 176 themselves.

The punctum plug 140 may be of a different size than punctum plug 40. In a representative but not limiting embodiment of punctum plug 140, the punctum plug 140 may be a "small" size punctum plug in which the punctum plug has an overall length of about 0.058 inch; the tip has a length of about 0.026 inch, a maximum external diameter of about 0.029 inch and a minimum external diameter of about 0.005 inch; the body has a length of about 0.027 inch and an external cross-sectional diameter of about 0.017 inch with the flared forward and rearward ends having a radius of curvature of about 0.003 inch; the passage has a length of about 0.043 inch and a diameter of about 0.0090 inch; the cap has a thickness of about 0.005 inch and a perimetrical edge about 0.029 inch in diameter with the annular border having a radius of curvature of about 0.005 inch; the perimeter of the opening is about 0.0090 inch in diameter; the recesses have a depth of about 0.001 inch; and the periphery of each recess has a major dimension of about 0.008 inch and a minor dimension of about 0.004 inch with the periphery of each recess being spaced along the proximal surface of the cap about 0.001 inch from the perimeter of the opening. The recesses 176 are arranged on the proximal surface 158 with their centers 182 spaced 90° from one another about central axis 166.

Figure 6:
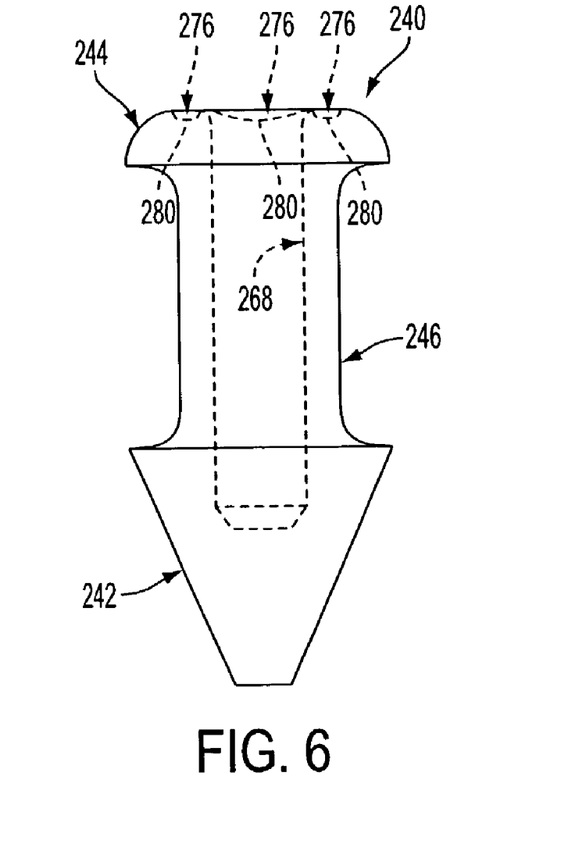
FIG. 6 is a side view of another alternative punctum plug according to the present invention.
Figure 7:
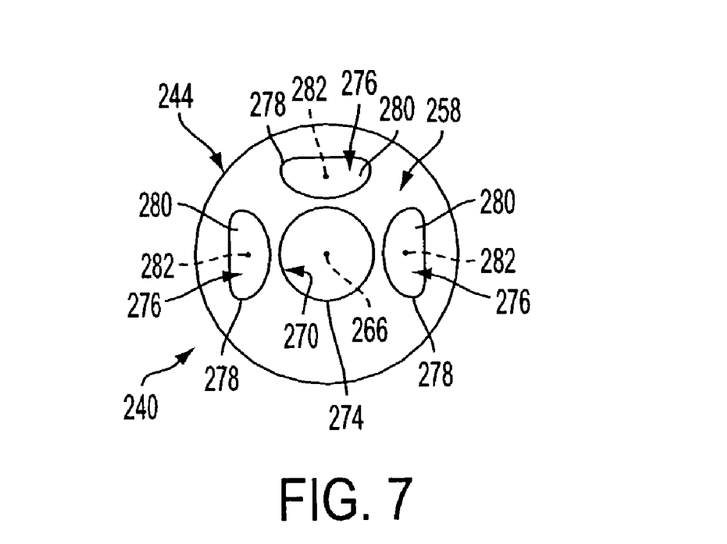
FIG. 7 is a top view of the punctum plug of FIG. 6.

Another alternative punctum plug according to the present invention is depicted at 240 in FIGS. 6 and 7. Punctum plug 240 is similar to punctum plugs 40 and 140 and comprises distal tip 242, proximal cap 244, body 246 and passage 268. Punctum plug 240 differs from punctum plugs 40 and 140 in that the proximal surface 258 of cap 244 has three recesses 276 separate and distinct from each other and from opening 270 of passage 268. Recesses 276 are each similar to recesses 76 and 176 and have centers 282 laterally offset from the central longitudinal axis 266 of punctum plug 240. Each recess 276 has the entire area circumscribed by its periphery 278 enclosed by the floor 280 of the recess. The entire periphery 278 of each recess 276 is disposed along proximal surface 258 outside of the perimeter 274 of opening 270 along proximal surface 258. Accordingly, the entirety of each recess 276 is not coextensive with and does not overlap the opening 270. Also, there is no overlap or coextensiveness between the peripheries 278 of the recesses 276 themselves.

The punctum plug 240 may be of a different size than the punctum plugs 40 and 140. In a representative but not limiting embodiment of punctum plug 240, the punctum plug 240 may be a "medium" size punctum plug in which the punctum plug has an overall length of about 0.063 inch; the tip has a length of about 0.031 inch, a maximum external diameter of about 0.033 inch and a minimum external diameter of about 0.005 inch; the body has a length of about 0.027 inch and an external cross-sectional diameter of about 0.020 inch with the flared forward and rearward ends of the body having a radius of curvature of about 0.003 inch; the passage has a length of about 0.043 inch and a diameter of about 0.0090 inch; the cap has a thickness of about 0.005 inch and a perimetrical edge about 0.033 inch in diameter with the annular border having a radius of curvature of about 0.005 inch; the perimeter of the opening is about 0.0090 inch; the recesses have a depth of about 0.001 inch, a major dimension of about 0.008 inch and a minor dimension of about 0.004 inch; and the periphery of each recess is spaced along the proximal surface of the cap about 0.001 inch from the perimeter of the opening. The recesses 276 are arranged on the proximal surface 258 with the centers 282 of the recesses spaced 90 degrees from one another about the central longitudinal axis 266.

Figure 8:
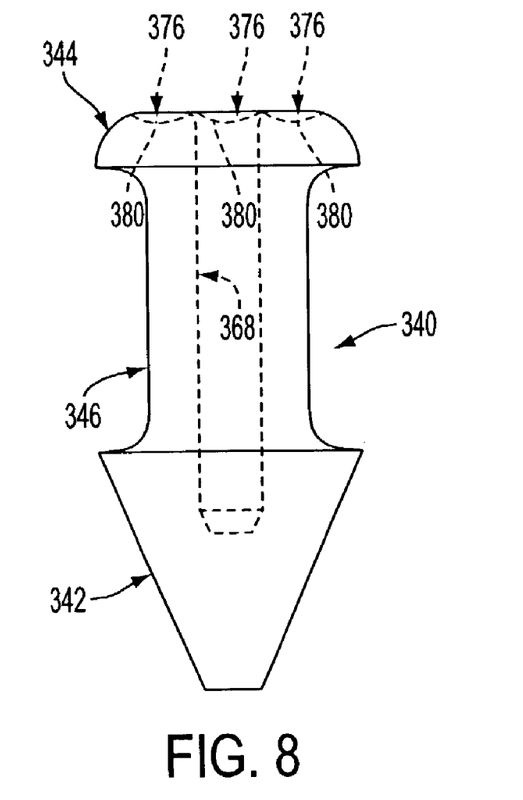
FIG. 8 is a side view of a further alternative punctum plug according to the present invention.
Figure 9:
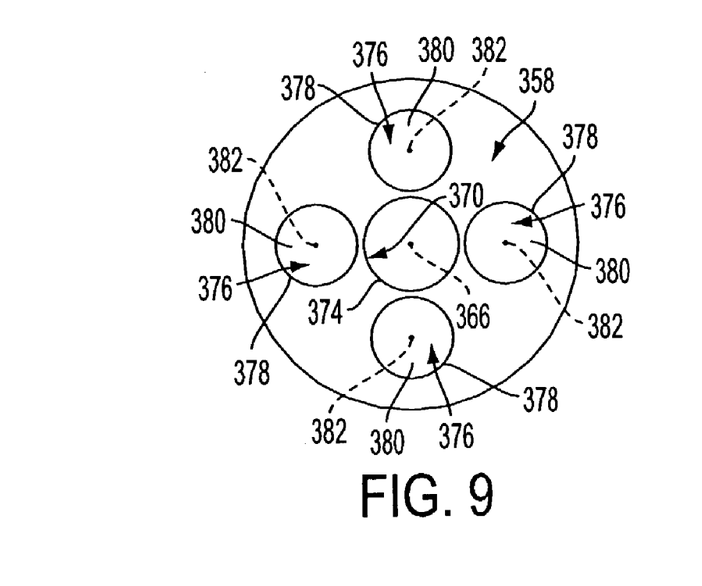
FIG. 9 is a top view of the punctum plug of FIG. 8.

An additional alternative punctum plug 340 according to the present invention is illustrated in FIGS. 8 and 9. Punctum plug 340 is similar to punctum plugs 40, 140 and 240 and comprises distal tip 342, proximal cap 344, body 346 and passage 368. Punctum plug 340 is different from punctum plugs 40, 140 and 240 in that the proximal surface 358 of cap 344 has four recesses 376 separate and distinct from each other and from opening 370 of passage 368. Recesses 376 are different from the recesses 76, 176 and 276 in that the periphery 378 of each recess 376 has a circular geometric configuration. The centers 382 for recesses 376 are laterally offset from the central longitudinal axis 366 of punctum plug 340. Each recess 376 has the entire area circumscribed by its periphery 378 enclosed by the floor 380 of the recess. The entire periphery 378 of each recess 376 is disposed along proximal surface 358 outside of the perimeter 374 of opening 370 along proximal surface 358. Accordingly, there is no overlap or coextensiveness between the opening 370 and the recesses 376. Also, there is no overlap or coextensiveness between the peripheries 378 of the recesses 376 themselves.

The punctum plug 340 may be of a different size than the punctum plugs 40, 140 and 240. In a representative but not limiting embodiment of punctum plug 340, the punctum plug 340 may be a "large" size punctum plug in which the punctum plug has an overall length of about 0.069 inch; the tip has a length of about 0.037 inch, a maximum external diameter of about 0.037 inch and a minimum external diameter of about 0.005 inch; the body has a length of about 0.027 inch and an external cross-sectional diameter of about 0.022 inch with the flared forward and rearward ends of the body having a radius of curvature of about 0.003 inch; the passage has a length of about 0.043 inch and a diameter of about 0.0090 inch; the cap has a thickness of about 0.005 inch and a perimetrical edge about 0.037 inch in diameter with the annular border having a radius of curvature of about 0.005 inch; the perimeter of the opening is about 0.0090 inch; the recesses have a depth of about 0.001 inch and a diameter of about 0.008 inch; and the periphery of each recess is spaced along the proximal surface of the cap about 0.001 inch from the perimeter of the opening. The recesses 376 are arranged on the proximal surface 358 with the centers 382 of the recesses spaced 90° from one another about the central longitudinal axis 366.

Punctum plugs 40, 140, 240, and 340 are microscopically sized in accordance with the microscopic size of the anatomical puncta and canaliculi. The punctum plugs 40, 140, 240 and 340 have first, second, third and fourth sizes, respectively, corresponding to different anatomical sizes of puncta and canaliculi. A punctum plug of the appropriate size can be thusly selected for implantation in the lacrimal drainage system of a patient's eye based upon the particular anatomical characteristics of the patient's lacrimal drainage system. Given the very small sizes of the punctum plugs, it is difficult to visually distinguish between different size punctum plugs. In the punctum plugs 40, 140, 240 and 340, the number of recesses 76, 176, 276 and 376, respectively, correspond to and are indicative of the size of the punctum plugs. More particularly, one recess in the proximal surface of the cap of the punctum plug identifies the punctum plug as an "extra small" size punctum plug; two recesses in the proximal surface of the cap of the punctum plug identifies the punctum plug as a "small" size punctum plug; three recess in the proximal surface of the cap of the punctum plug identifies the punctum plug as a "medium" size punctum plug; and four recesses in the proximal surface of the cap of the punctum plug identifies the punctum plug as a "large" size punctum plug. The size of a punctum plug can thusly be identified or ascertained visually merely by viewing the cap of the punctum plug, as typically assisted with microscopic magnification, and noting the number of recesses in the cap. The size of a punctum plug can be determined in this manner prior or subsequent to implantation in that subsequent to implantation the exposed cap of the punctum plug can be visualized microscopically while the punctum plug remains implanted.

With the punctum plugs of the present invention, tear fluid is retained in the fluid collecting recesses of the caps to assist in keeping the corneal surface wetted and to reduce possible lid sensation from exposure of the caps in the eye. Tear fluid is collected in and adheres to the recesses by surface tension of the tear fluid with the silicone rubber (LSR) from which the punctum plugs are made. Tear fluid is collected along the proximal surfaces of the caps so as to be exposed in the eye for enhanced wetting and lubrication. The number of recesses in the caps allow the size of the punctum plugs to be identified visually, and the size of an implanted punctum plug can be visually identified by noting the number of recesses without removing the implanted punctum plug from the eye.

The distal tips can have various external configurations and/or external cross-sections to facilitate advancement of the punctum plugs during implantation and to resist withdrawal of the punctum plugs following implantation. The perimetrical edges the caps can have various geometric configurations to provide occlusion of the punctum while preventing passage of the caps through the punctal openings. The caps may be designed so that the caps are partly disposed within the punctal opening upon implantation. The bodies can have various external cross-sectional configurations which may be uniform or constant along the length of the bodies or non-uniform or non-constant along the length of the bodies. The passages can have various cross-sectional configurations depending on the configuration of the insertion tools, and the passage cross-sections can be uniform or non-uniform along the length of the passages. The length of the passages can vary depending on the length of the insertion tools to be engaged with the passages. The perimeters of the passage openings on the proximal surfaces of the caps can have various configurations. The peripheries of the recesses can have various geometric configurations including, but not limited to, semi-circular, partial-circular, circular, square, rectangular, triangular, quadrangular, trapezoidal, oval and elliptical configurations. The recesses can be arranged on the proximal surfaces in various ways.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A punctum plug for implantation in the lacrimal drainage system of the eye, comprising
   a proximal cap having a proximal surface and a distal surface;
   a distal tip;
   a body connecting said cap to said tip, said distal tip being insertable through the punctal opening of the lacrimal drainage system and into the canalicular canal communicating with the punctal opening to seat said cap on the punctal opening with said proximal surface exposed in the eye; and
   one or more recesses in said proximal surface each having a center laterally offset from a central longitudinal axis of said punctum plug for retaining tear fluid.

2. The punctum plug recited in claim 1 wherein said cap is of a size to occlude the punctal opening.

3. The punctum plug recited in claim 2 wherein said cap is of a size to prevent passage of said cap through the punctal opening.

4. The punctum plug recited in claim 1 wherein said tip comprises an anchor to resist withdrawal from the canalicular canal.

5. The punctum plug recited in claim 1 wherein each of said one or more recesses has a periphery of partial circular configuration along said proximal surface.

6. The punctum plug recited in claim 1 wherein each of said one or more recesses has a periphery of circular configuration along said proximal surface.

7. The punctum plug recited in claim 1 wherein said one or more recesses comprises one to four recesses.

8. A punctum plug for implantation in the lacrimal drainage system of the eye, comprising
   a proximal cap having a proximal surface and a distal surface;
   a distal tip;
   a body connecting said cap to said tip, said distal tip being insertable through the punctal opening of the lacrimal drainage system and into the canalicular canal communicating with the punctal opening to seat said cap on the punctal opening with said proximal surface exposed in the eye;
   a passage in said punctum plug for releasable engagement with an insertion tool, said passage having an opening along said proximal surface; and
   one or more recesses in said proximal surface for retaining tear fluid, each of said one or more recesses having a periphery along said proximal surface and a floor joined to said proximal surface along said periphery, the entire area within said periphery being enclosed by said floor.

9. The punctum plug recited in claim 8 wherein said passage is coaxial with a central longitudinal axis of said punctum plug and each of said one or more recesses has a center laterally offset from said central longitudinal axis.

10. The punctum plug recited in claim 8 wherein said passage terminates in said tip.

11. The punctum plug recited in claim 8 wherein said punctum plug is made from a medically acceptable silicone rubber.

12. The punctum plug recited in claim 8 wherein each of said one or more recesses has a depth of about 0.001 inch.

13. The punctum plug recited in claim 8 wherein said opening has a perimeter along said proximal surface and said periphery of each of said one or more recesses is disposed in its entirety outside of said perimeter.

14. A punctum plug for implantation in the lacrimal drainage system of the eye, comprising
   a proximal cap having a proximal surface and a distal surface;
   a distal tip;
   a body connecting said cap to said tip, said tip being insertable through the punctal opening of the lacrimal drainage system and into the canalicular canal communicating with the punctal opening to seat said cap on the punctal opening with said proximal surface exposed in the eye; and
   one or more recesses in said proximal surface, the number of said recesses in said proximal surface corresponding to a size of said punctum plug.

15. The punctum plug recited in claim 14 wherein said number of said recesses is one recess where said punctum plug is a first size, said number of said recesses is two recesses where said punctum plug is a second size, different from said first size, said number of said recesses is three recesses where said punctum plug is a third size, different from said first size and said second size, and said number of said recesses is four recesses where said punctum plug is a fourth size, different from said first size, said second size and said third size.

16. The punctum plug recited in claim 15 wherein said first size is smaller than said second size, said second size is smaller than said third size and said third size is smaller than said fourth size.

17. The punctum plug recited in claim 14 and further including a passage in said punctum plug coaxial with a central longitudinal axis of said punctum plug, said passage having an opening along said proximal surface, wherein each of said one or more recesses is separate and distinct from said opening.

18. A method of punctal occlusion for the lacrimal drainage system of the eye, comprising the steps of
   releasably engaging an insertion tool in an insertion passage of a punctum plug having a distal tip, a proximal cap and a body connecting the distal to the proximal cap with the insertion passage extending distally in the punctum plug from an opening along a proximal surface of the cap;
   introducing the distal tip in a punctal opening of the lacrimal drainage system;
   advancing the punctum plug in the punctal opening to anchor the tip in the canalicular canal communicating with the punctal opening and to seat the cap on the punctal opening with the proximal surface exposed in the eye;
   disengaging the insertion tool from the opening and withdrawing the insertion tool from the eye;
   leaving the punctum plug in place to block drainage of tear fluid from the eye;
   collecting tear fluid in one or more recesses in the proximal surface in which the entirety of each recess is non-overlapping with the opening; and
   adhering the tear fluid in the one or more recesses by surface tension.

19. The method recited in claim 18 wherein said step of leaving includes anchoring the punctum plug in place via engagement of the tip with the anatomical wall of the canalicular canal.

20. The method recited in claim 18 wherein said step of advancing includes limiting advancement of the punctum plug via engagement of the cap with an anatomical rim of the punctal opening.

21. The method recited in claim 18 and further including, subsequent to said step of leaving, the steps of visualizing the proximal surface exposed in the eye, noting the number of the one or more recesses in the proximal surface and identifying the size of the punctum plug from the number of the recesses.

* * * * *